(12) United States Patent
Mason et al.

(10) Patent No.: US 12,109,215 B2
(45) Date of Patent: Oct. 8, 2024

(54) COMBINATION THERAPIES FOR INHIBITION OF POLO-LIKE KINASE 4

(71) Applicant: UNIVERSITY HEALTH NETWORK, Toronto (CA)

(72) Inventors: Jacqueline M. Mason, Toronto (CA); Mark R. Bray, Oakville (CA); Tak Wah Mak, Toronto (CA); Graham Fletcher, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 458 days.

(21) Appl. No.: 16/644,633

(22) PCT Filed: Sep. 7, 2018

(86) PCT No.: PCT/CA2018/051086
§ 371 (c)(1),
(2) Date: Mar. 5, 2020

(87) PCT Pub. No.: WO2019/046949
PCT Pub. Date: Mar. 14, 2019

(65) Prior Publication Data
US 2021/0060026 A1    Mar. 4, 2021

Related U.S. Application Data

(60) Provisional application No. 62/555,718, filed on Sep. 8, 2017.

(51) Int. Cl.
*A61K 31/5377* (2006.01)
*A61K 39/395* (2006.01)
*A61P 35/00* (2006.01)

(52) U.S. Cl.
CPC ...... *A61K 31/5377* (2013.01); *A61K 39/3955* (2013.01); *A61P 35/00* (2018.01)

(58) Field of Classification Search
CPC ............ A61K 31/5377; A61K 39/3955; A61K 45/06; A61K 2300/00; A61K 2039/505; A61P 35/00; C07D 413/14
See application file for complete search history.

(56) References Cited

U.S. PATENT DOCUMENTS

2013/0123273 A1    5/2013    Pan et al.

FOREIGN PATENT DOCUMENTS

| CA | 2803446 A1 | 1/2012 |
| CA | 2926845 A1 | 4/2015 |

(Continued)

OTHER PUBLICATIONS

Jiang et al., "T-cell exhaustion in the tumor microenvironment," Cell Death and Disease 6, e1792; pp. 1-9 (Year: 2015).*

(Continued)

*Primary Examiner* — Kortney L. Klinkel
*Assistant Examiner* — Gabrielle A Small
(74) *Attorney, Agent, or Firm* — McCarter & English, LLP; Steven G. Davis; Wei Song

(57) ABSTRACT

Provided herein are methods of treating cancer using an effective amount of a compound represented by the formula (Formula (I)) or a pharmaceutically acceptable salt thereof and an effective amount of an immune checkpoint inhibitor. Also provided are compositions comprising the same compound represented by the formula shown above or a pharmaceutically acceptable salt thereof and an immune checkpoint inhibitor.

8 Claims, 9 Drawing Sheets

(56) References Cited

FOREIGN PATENT DOCUMENTS

| CA | 2963281 A1 | 4/2016 | | |
|---|---|---|---|---|
| CA | 2975729 A1 | 8/2016 | | |
| CN | 102892766 A | 1/2013 | | |
| CN | 105764515 A | 7/2016 | | |
| CN | 105764899 A | 7/2016 | | |
| WO | WO-2012048411 A1 | * | 4/2012 | ............ A61P 35/00 |
| WO | 2015/193212 A1 | 12/2015 | | |
| WO | 2016/130297 A2 | 8/2016 | | |

OTHER PUBLICATIONS

Mason et al., "Functional characterization of CFI-402257, a potent and selective Mps1/TTK kinase inhibitor, for the treatment of cancer," PNAS (114)12 pp. 3127-3132 (Year: 2017).*

Mason et al., "Functional Characterization of CFI-400945 a Polo-like Kinase 4 Inhibitor as a Potential Anticancer Agent," Cancer Cell 26, pp. 163-176 (Year: 2014).*

Dominguez-Brauer et al., "Targeting Mitosis in Cancer: Emerging Strategies," Molecular Cell 60, pp. 524-536 (Year: 2015).*

Domcheck et al., "A phase I/II, open-label trial of olaparib in combination with durvalumab (MEDI4736) in patients (pts) with advanced solid tumours," Annals of Oncology 27 (Supplement 6): pp. vi359-vi378 (Year: 2016).*

Llosa et al The Vigorous Immune Microenvironment of Microsatellite Instable Colon Cancer Is Balanced by Multiple Counter-Inhibitory Checkpoints Cancer Discov (2015) 5 (1): 43-51 (Year: 2015).*

Kwok et al Pembrolizumab (Keytruda) Human Vaccines & Immunotherapeutics (2016)12(11): 2777-2789. (Year: 2016).*

Li et al A Mini-Review for Cancer Immunotherapy: Molecular Understanding of PD-1/PD-L1 Pathway & Translational Blockade of Immune Checkpoints. Int. J. Mol. Sci. (2016) 17 1151 (Year: 2016).*

Kazazian et al., Polo-Like Kinases in Colorectal Cancer: Potential for Targeted Therapy. Curr Colorectal Cancer Rep. 2015;11:187-199.

Sampson et al., The Discovery of Polo-Like Kinase 4 Inhibitors: Identification of (1R,2S)?2-(3-((E)?4-(((cis)?2,6-Dimethylmorpholino)methyl)styryl)? 1H?indazol-6-yl)-5 !-methoxyspiro[cyclopropane-1,3 !-indolin]-2 !-one (CFI-400945) as a Potent, Orally Active Antitumor Agent. J Med Chem. 2014;58:147-69.

Wouters et al., The Summit for Cancer Immunotherapy (Summit4CI), Jun. 26-29, 2016 Halifax, Canada. Cancer Immunol Immunother. Jun. 2017;66(6):811-818.

International Search Report and Written Opinion for Application No. PCT/CA2018/051086, dated Nov. 30, 2018, 9 pages.

Holland et al., Polo-like kinase 4 inhibition: a strategy for cancer therapy? Cancer Cell. Aug. 11, 2014;26(2):151-3.

Lu Heng, The 418 Questions that Cancer Patients are Most Concerned About. Hubei Science and Technology Press. 3 pages, Oct. 31, 2015.

Chinese Office Action for Application No. 201880067175.0, dated Mar. 23, 2023, 9 pages.

* cited by examiner

COMBINATION THERAPIES FOR INHIBITION OF POLO-LIKE KINASE 4

CROSS REFERENCE TO RELATED APPLICATIONS

This application is a U.S. national stage application filed under 35 U.S.C. § 371(c), of International Application No. PCT/CA2018/051086, filed on Sep. 7, 2018, which claims the benefit of priority of U.S. Provisional Patent Application No. 62/555,718, filed Sep. 8, 2017. The entire teachings of each of the aforementioned applications are incorporated herein by reference.

BACKGROUND

CFI-400945 is a compound represented by the formula:

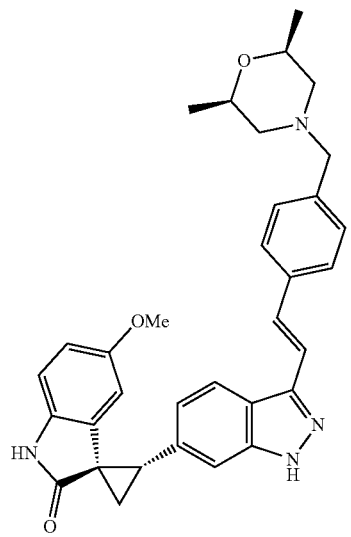 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

that inhibits Polo-like Kinase 4 (PLK4) activity. PLK4 is a conserved key regulator of centriole duplication, and is aberrantly expressed in several human tumors. Dysregulation of PLK4 expression causes loss of centrosome numeral integrity, which promotes genomic instability, but could also enable cancer cells to tolerate its effects. Further disruption of centriole duplication by inhibition of PLK4 activity could exacerbate the genomic instability in cancer cells and force their death.

CFI-400945 is presently undergoing a phase I clinical trial (ClinicalTrials.gov ID NCT01954316) with patients having advanced cancers. Given the potency and selectivity of CFI-400945 in inhibiting an important mitotic regulatory enzyme, it would be advantageous to further enhance the efficacy of this drug candidate in cancer treatment.

SUMMARY

It has now been found by the inventors of the present application that the administration of the compound CFI-400945 or a pharmaceutically acceptable salt thereof and an immune checkpoint inhibitor synergistically treats cancer. See e.g., FIGS. 1D, 1F, 1H, which illustrate complete tumor regression in the syngeneic CT26 mouse colon carcinoma model upon administration of a combination of a pharmaceutically acceptable salt of the compound CFI-400945 and the rat IgG2a anti-PD-1 antibody, at various dosages.

Importantly, when the animals in which complete tumor regression has occurred are re-challenged by inoculation with the same cancer cells, tumors do not grow in any of these animals, thereby indicating that immunity to the cancer cells had been generated by the CFI-400945-anti-PD-1-antibody combination therapy. Furthermore, animals that are subjected to this combination therapy do not suffer from any significant body weight loss, thereby indicating that both agents at at least the administered dosages are well-tolerated.

Based on these results, provided herein are methods of treating cancer in a subject, by administering to the subject an effective amount of the compound CFI-400945 or a pharmaceutically acceptable salt thereof and an effective amount of immune checkpoint inhibitor as described herein.

Also provided herein are pharmaceutical compositions comprising the compound CFI-400945 or a pharmaceutically acceptable thereof and an immune checkpoint inhibitor as described herein.

DETAILED DESCRIPTION

Figure 1A:
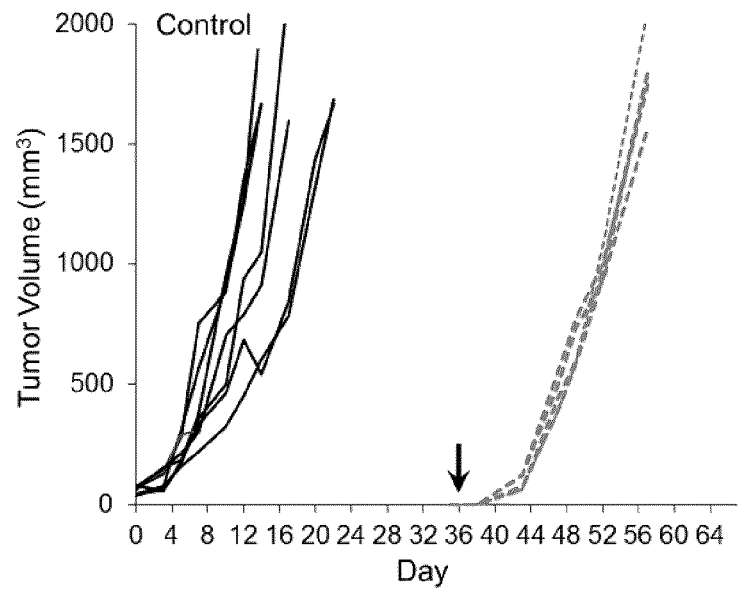
FIG. 1A illustrates change in CT26 tumor volume in Balb/cJ mice, inoculated with CT26 cells on either Day −7 or 36, that receive rat IgG2a isotype control.

In one aspect, the present disclosure provides a method of treating cancer in a subject, comprising the step of administering to the subject an effective amount of the compound CFI-400945 that is represented by the formula:

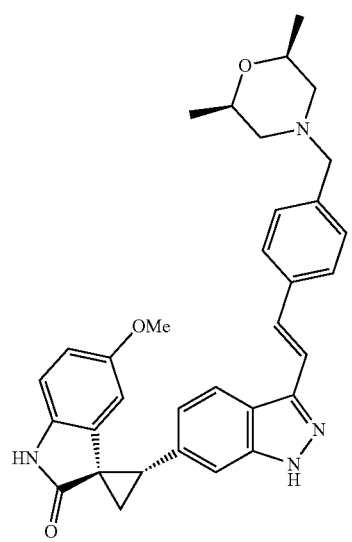 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

or a pharmaceutically acceptable salt thereof and an effective amount of an immune checkpoint inhibitor.

It will be understood that unless otherwise indicated, the administrations described herein include administering the described compound CFI-400945 or a pharmaceutically acceptable salt thereof prior to, concurrently with, or after administration of the immune checkpoint inhibitor described herein. Thus, simultaneous administration is not necessary for therapeutic purposes. In one embodiment, however, the compound CFI-400945 or a pharmaceutically acceptable salt thereof is administered concurrently with the immune checkpoint inhibitor.

The compound CFI-400945 described herein has basic amine groups and therefore can form pharmaceutically acceptable salts with pharmaceutically acceptable acid(s). Accordingly, the term "pharmaceutically acceptable salt" as used herein refers to any suitable pharmaceutically acceptable acid addition salt of the compound CFI-400945 described herein, which includes but is not limited to salts of inorganic acids (e.g., hydrochloric acid, hydrobromic, phosphoric, nitric, and sulfuric acids) and of organic acids (such as, acetic acid, trifluoroacetic acid, fumaric, benzenesulfonic, benzoic, methanesulfonic, and p-toluenesulfonic acids). Other examples of such salts include hydrochlorides, hydrobromides, sulfates, methanesulfonates, nitrates, benzoates, trifluoroacetates, fumarates and salts with amino acids such as glutamic acid.

As used herein, an "immune check point inhibitor" or simply a "checkpoint inhibitor" refers to any compound that, either directly or indirectly, decreases the level of or inhibits the function of an immune checkpoint receptor protein found on the surface of an immune cell (e.g., T-cells, B-cells, etc.). Alternatively, the immune checkpoint inhibitor is a compound that, either directly or indirectly, decreases the level of or inhibits the function of a ligand on the surface of an immune cell-inhibitory cell (e.g., regulatory T-cells, tolerogenic antigen presenting cells (APC), myeloid-derived suppressor cells (MDSC), tumor-associated macrophages (TAM), cancer-associated fibroblasts (CAF), other cancer cells and APCs, etc.), or secreted by an immune cell-inhibitory cell. This ligand is typically capable of binding the immune checkpoint receptor protein of the immune cell. A non-limiting example of an immune checkpoint receptor protein-ligand pair is PD-1/PD-L1. PD-1 is an immune checkpoint receptor protein found on T-cells. PD-L1 that is often over-expressed by cancer cells binds to PD-1 and helps the cancer cells evade the host immune system attack. Accordingly, an immune checkpoint inhibitor prevents or reverses this PD-1/PD-L1 binding, by either blocking the PD-1 on the T-cells (i.e., a PD-1 inhibitor) or the PD-L1 on the cancer cells (i.e., a PD-L1 inhibitor), thereby maintaining or restoring anti-tumor T-cell activity or blocking T-cell-inhibitory cell activity. Additionally, an immune checkpoint inhibitor refers to a compound as described in US Patent Application Publication Nos. US 2017/0190675 and US 2016/0185870, and International Patent Application Publication Nos. WO 2015/112900, WO 2010/027828 and WO 2010/036959.

An immune checkpoint inhibitor in accordance with the present invention may be a small-molecule organic compound or a large molecule such as a peptide or a nucleic acid. In at least one embodiment, an immune checkpoint inhibitor is an antibody or an antigen binding fragment thereof. In at least one embodiment, an immune checkpoint inhibitor is a monoclonal antibody or an antigen binding fragment thereof.

As used herein, the term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc In some embodiments, an antibody is a non-naturally occurring antibody. In some embodiments, an antibody is purified from natural components. In some embodiments, an antibody is recombinantly produced. In some embodiments, an antibody is produced by a hybridoma.

The term "antibody fragment" refers to a portion of an intact antibody and refers to the antigenic determining variable regions of an intact antibody. Examples of antibody fragments include, but are not limited to, Fab, Fab', F(ab')$_2$, and F$_v$ fragments, linear antibodies, single chain antibodies, and multispecific antibodies formed from antibody fragments. The term "antigen-binding fragment" of an antibody includes one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding fragment" of an antibody include (without limitation): (i) an Fab fragment, a monovalent fragment consisting of the $V_L$, $V_H$, $C_L$, and $C_{H1}$ domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fa fragment consisting of the $V_H$ and $C_{H1}$ domains (i.e., that portion of the heavy chain which is included in the Fab); (iv) a F$_v$ fragment consisting of the $V_L$ and $V_H$ domains of a single arm of an antibody, and the related disulfide linked F$_v$; (v) a dAb (domain antibody) or sdAb (single domain antibody) fragment (Ward et al., Nature 341:544-546, 1989), which consists of a $V_H$ domain; and (vi) an isolated complementarity determining region (CDR).

As used herein, a "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (e.g., Fab, Fab', F(ab')$_2$, F$_v$), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, hamster) that have the desired specificity, affinity, and capability (Jones et al., Nature 321:522-525, 1986; Riechmann et al., Nature 332:323-327, 1988; Verhoeyen et al., Science 239:1534-1536, 1988).

A non-exhaustive list of examples of an immune checkpoint inhibitor is provided as following: a CD40L inhibitor, a DR3 inhibitor, a TL1A inhibitor, a GITR inhibitor, a GITRL inhibitor, a 4-1BB inhibitor, a 4-1BBL inhibitor, an OX40 inhibitor, an OX40L inhibitor, a CD27 inhibitor, a CD70 inhibitor, a TMIGD2 inhibitor, an HHLA2 inhibitor, an ICOS inhibitor, an ICOSL inhibitor, a B7RP1 inhibitor, a CD28 inhibitor, a PD-1 inhibitor, a PD-L1 inhibitor, a PD-L2 inhibitor, a CTLA-4 inhibitor, a CD80 inhibitor, a CD86 inhibitor, a KIR inhibitor, a TCR inhibitor, a LAG3 inhibitor, an MHCI inhibitor, an MHCII inhibitor, a CD80 inhibitor, a TIM-3 inhibitor, a GALS inhibitor, a BTLA inhibitor, an HVEM inhibitor, a CD160 inhibitor, a CD137 inhibitor, a CD137L inhibitor, a LIGHT inhibitor, a phosphatidylserine inhibitor, a VISTA inhibitor, a BTNL2 inhibitor, a B7-H3 inhibitor and a B7-H4 inhibitor. In certain embodiments, the immune checkpoint inhibitor applied in a cancer treatment method of the invention is one or more selected from the aforementioned examples.

In one embodiment, the immune checkpoint inhibitor is one or more selected from a PD-1 inhibitor, a PD-L1 inhibitor and a CTLA-4 inhibitor.

In one embodiment, the immune checkpoint inhibitor is a PD-1 inhibitor. In another embodiment, the immune checkpoint inhibitor is a PD-L1 inhibitor.

In some embodiments, the immune checkpoint inhibitor is one or more selected from pembrolizumab, ipilimumab, nivolumab, atezolizumab, avelumab and durvalumab.

In some embodiments, the immune checkpoint inhibitor is one or more selected from JS001, SHR-1210, BGB-A317, IBI-308, REGN2810, JS003, SHR-1316, KN035, BMS-936559, LAG525, BMS-986016, MBG453, MEDI-570, OREG-103/BY40 and lirilumab. In one embodiment, the immune checkpoint inhibitor is one or more selected from CJS001, SHR-1210, BGB-A317, IBI-308 and REGN2810. In an alternative embodiment, the immune checkpoint inhibitor is one or more selected from JS003, SHR-1316, KN035 and BMS-936559.

As used herein, the terms "treatment," "treat," and "treating" refer to reversing, alleviating, ameliorating, inhibiting or slowing the progression of a cancer, reducing the likelihood of recurrence of a cancer, or one or more symptoms thereof, as described herein. Exemplary types of cancer treated by the methods and compositions of the invention include but are not limited to breast cancer (including metastatic breast cancer); colon cancer; rectal cancer; colorectal cancer; lung cancer (including small-cell lung cancer (SCLC), non-small cell lung cancer (NSCLC), adenocarcinoma of the lung, and squamous carcinoma of the lung); cancer of the peritoneum; gastric or stomach cancer; gastrointestinal cancer; cervical cancer; liver cancer; bladder cancer; hepatoma; ovarian cancer; endometrial or uterine cancer; prostate cancer; testicular cancer; leukemias; lymphomas; hematological malignancies; brain cancer (including glioma, glioblastoma multiforme, medulloblastoma, and neuroblastoma); head and neck cancer; pancreatic cancer; melanoma; hepatocellular cancer; kidney or renal cancer; vulval cancer; thyroid cancer; hepatic carcinoma; anal carcinoma; penile carcinoma; Merkel cell cancer; mycoses fungoids; esophageal cancer; tumors of the biliary tract; salivary gland cancer; sarcomas; retinoblastoma; liposarcoma, synovial cell sarcoma; neuroendocrine tumors; gastrinoma; islet cell cancer; mesothelioma; schwannoma; acoustic neuroma; meningioma; adenocarcinoma; squamous cell cancer and epithelial squamous cell cancer. In another embodiment, the cancer treated by the methods and compositions of the invention is pancreatic cancer, lung cancer, breast cancer, colon cancer, brain cancer, neuroblastoma, prostate cancer, melanoma, glioblastoma multiforme, ovarian cancer, lymphoma, leukemia, melanoma, sarcoma, paraneospasia, osteosarcoma, germinoma, glioma or mesothelioma. In yet another embodiment, the cancer is renal cell carcinoma, non-small cell lung cancer, urothelial cancer, head and neck cancer, ovarian cancer, lymphoma, melanoma, pancreatic cancer, myeloma, acute myeloid leukemia, bladder cancer and Hodgkin's lymphoma.

The term "an effective amount" means an amount when administered to a subject which results in beneficial or desired results, including clinical results, i.e., reversing, alleviating, inhibiting or slowing the progression of a cancer, reducing the likelihood of recurrence of a cancer, or one or more symptoms thereof, e.g., as determined by clinical symptoms, the amount or volume or cancer cells or tumors in a subject compared to a control.

In an embodiment, an effective amount of the compound CFI-400945 or a pharmaceutically acceptable salt thereof taught herein ranges from about 0.1 to about 1000 mg/kg body weight, alternatively about 1 to about 500 mg/kg body weight, and in another alternative, from about 1 to about 100 mg/kg body weight, and in yet another alternative, from about 1 to about 50 mg/kg, and in yet another alternative, from about 0.1 to about 10 mg/kg body weight, and in yet another alternative from about 1 to about 7 mg/kg body weight or about 1 to about 6.5 mg/kg body weight if administered daily. In an embodiment, an effective amount of an immune checkpoint inhibitor taught herein ranges from about 0.01 to about 1000 µg/kg body weight, alternatively from about 0.05 to about 500 µg/kg body weight. The skilled artisan will appreciate that certain factors may influence the dosage required to effectively treat a subject suffering from cancer or reduce the likelihood of recurrence of a cancer. These factors include, but are not limited to, the classification and/or severity of the disease or disorder, previous treatments, the general health and/or age of the subject and other diseases present.

In another aspect, pharmaceutical compositions comprising the compound CFI-400945 or a pharmaceutically acceptable salt thereof and an immune checkpoint inhibitor are also included in the present disclosure.

Also included are the use of the compound CFI-400945 or a pharmaceutically acceptable salt thereof in the manufacture of a medicament to be used in combination with an immune checkpoint inhibitor as described herein for the treatment of one or more cancers described herein. Also included herein are pharmaceutical compositions comprising the compound CFI-400945 or a pharmaceutically acceptable salt thereof and an immune checkpoint inhibitor as described herein optionally together with a pharmaceutically acceptable carrier, in the manufacture of a medicament for the treatment of one or more cancers described herein. Also included is the compound CFI-400945 for use in combination with an immune checkpoint inhibitor as described herein for the treatment of a subject with cancer. Further included are pharmaceutical compositions comprising the compound CFI-400945 or a pharmaceutically acceptable salt thereof and an immune checkpoint inhibitor as described herein, optionally together with a pharmaceutically acceptable carrier, for use in the treatment of one or more cancers described herein. Further included are pharmaceutical compositions comprising the compound CFI-400945 or a pharmaceutically acceptable salt thereof and an immune checkpoint inhibitor as described herein optionally together with a pharmaceutically acceptable carrier for use in the treatment of one or more cancers described herein.

The term "pharmaceutically acceptable carrier" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulose, polyacrylates, waxes, polyethylene-polyoxypropylene-block polymers, polyethylene glycol and wool fat.

Other excipients, such as flavoring agents; sweeteners; and preservatives, such as methyl, ethyl, propyl and butyl parabens, can also be included. More complete listings of suitable excipients can be found in the Handbook of Pharmaceutical Excipients (5th Ed., a Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003, 20th edition) and in The United States Pharmacopeia: The National Formulary (USP 24 NF19) published in 1999.

The compound CFI-400945 or a pharmaceutically acceptable salt thereof and the immune checkpoint inhibitor, or the compositions of the present teachings may be administered, for example, by oral, parenteral, sublingual, topical, rectal, nasal, buccal, vaginal, transdermal, patch, pump administration or via an implanted reservoir, and the pharmaceutical compositions would be formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

Other forms of administration included in this disclosure are as described in WO 2013/075083, WO 2013/075084, WO 2013/078320, WO 2013/120104, WO 2014/124418, WO 2014/151142, and WO 2015/023915, the contents of which are incorporated herein by reference.

EXEMPLIFICATION

While we have described a number of embodiments of this invention, it is apparent that our basic examples may be altered to provide other embodiments that utilize the compounds and methods of this disclosure. Therefore, it will be appreciated that the scope of this disclosure is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

Example 1

Materials

Salt forms of the compound CFI-400945 were prepared using the one or more of the procedures described in U.S. Pat. Nos. 8,269,596; 8,481,533; 8,921,545; 9,139,563 and 9,579,327; International Patent Application Publication No. WO 2015/054793; and Sampson et al. (2015) *J. Med. Chem.* 58(1):147-169. The fumarate salt form of the compound CFI-400945 was used in all of the studies described herein.

Rat IgG2a anti-PD-1 antibody (clone RMP1-14; cat. no. BE0146) and rat IgG2a isotype control (clone 2A3; cat. no. BE0089) were obtained from Bio X Cell.

BALB/cJ mice were obtained from The Jackson Laboratory. C56BL/6 mice were obtained from the animal colony at the Ontario Cancer Institute of the University Health Network (Toronto, Canada). Six- to eight-week-old female animals were used for all of the studies described herein and were allowed unrestricted access to food and water. All animal procedures were approved by the institutional animal care and use committee of the University Health Network (Toronto, Canada).

CT26 is a murine colon carcinoma cell line derived from a BALB/c mouse, and was obtained from American Type Culture Collection (ATCC) and maintained according to the supplier's instructions. MC38 is a murine colon carcinoma cell line derived from a C57BL/6 mouse, and was obtained from a collaborator (Toronto, Canada) and maintained according to the supplier's instructions.

Short tandem repeat (STR) profiling was used to verify authenticity of the cell lines. Sixteen STR loci were simultaneously amplified in multiplex PCR at The Centre for Applied Genomics (Toronto), and the ATCC database was used for comparison when possible Cell lines were routinely tested for *mycoplasma* and used at low passage numbers (<15).

Example 2

Methods

BALB/cJ mice were inoculated subcutaneously with $1\times10^6$ CT26 cells, and C57BL/6 mice were inoculated subcutaneously with $0.5\times10^6$ MC38 cells. The mice were then randomized. Animal weights were monitored daily, and tumor volume was measured three times per week.

Tumor volume (in cubic millimeters or $mm^3$) was defined as $100\times[1-TV_{f,treated}-TV_{i,treated})/(TV_{f,control}-TV_{i,control})]$, where $TV_f$ is the average tumor volume at the end of study and $TV_i$ is the average tumor volume at the end initiation of treatment. In cases in which tumor regression occurred, percentage of tumor regression was defined as $100\times[1-(TV_{f,treated}/TV_{i,treated})]$. At the completion of each study, the mice were killed by an anesthetic overdose, and tumor tissue was removed for further analysis.

Treatments were initiated when tumor volumes reached an average size of ~60 $mm^3$. To treat an established CT26 or MC38 tumor, the animals were first assigned into groups, i.e., the control group receiving rat IgG2a isotype control, the group receiving the compound CFI-400945 monotherapy, the group receiving the rat IgG2a anti-PD-1 antibody monotherapy and the group receiving the combination therapy.

The compound CFI-400945 and the vehicle (water) were administered by oral gavage (PO), at one of the following dosages: (i) 6.5 mg/kg once daily (QD) for 21 days; (ii) 13 mg/kg twice a week (BIW or 2 on/5 off) for 21 days; (iii) 52 mg/kg once weekly (QW) for 21 days; and (iv) 104 mg/kg in two doses, i.e., on Days 0 and 14.

The anti-PD-1 antibody or the isotype control were administered by intraperitoneal (IP) injection. 150 µg anti-PD-1 antibody was administered in four doses, i.e., on Days 0, 3, 6 and 10.

Example 3

Complete Regression in Combination CFI-400945 and Anti-PD-1-Antibody-Treated CT26 Tumors The size of each individual CT26 tumor within each treatment arm is plotted (See FIGS. 1A-1J). As can be seen in FIG. 1A, tumors in the vehicle-treated control arm grew rapidly, and the average tumor was >1500 $mm^3$ by Day 11 of treatment.

Figure 1B:
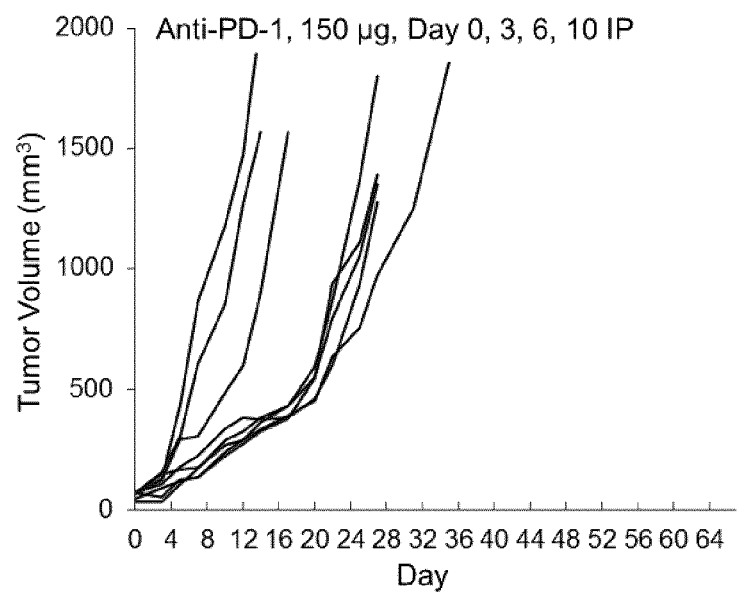
FIG. 1B illustrates change in CT26 tumor volume in Balb/cJ mice that received 150 μg of rat IgG2a anti-PD-1 antibody on Days 0, 3, 6 and 10.

As shown in FIG. 1B, there was tumor growth delay in the anti-PD-1-antibody-treated single agent arms. The administered anti-PD-1-antibody dosage of 150 µg on Days 0, 3, 6 and 10 was well-tolerated, as indicated by a lack of any significant body weight loss (data not shown) or any animal death. However, although there was tumor growth inhibition in the anti-PD-1 antibody monotherapeutic arms, there were no instances in which complete regression was observed.

Figure 1C:
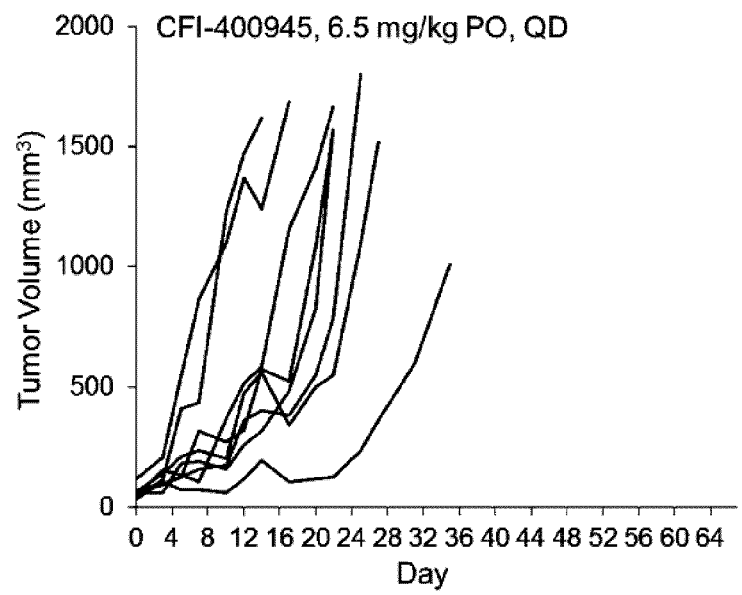
FIG. 1C illustrates change in CT26 tumor volume in Balb/cJ mice that received 6.5 mg/kg of CFI-400945 once daily for 21 days.

Similarly, the CFI-400945-treated single agent arms in FIG. 1C indicate tumor growth delay. The administered CFI-400945 daily dosage of 6.5 mg/kg daily for 21 days in these plots was well-tolerated, as indicated by a lack of any significant body weight loss (data not shown) or any animal death. However, although there was tumor growth inhibition in these CFI-400945 monotherapeutic arms, there were no instances in which complete regression was observed.

Figure 1D:
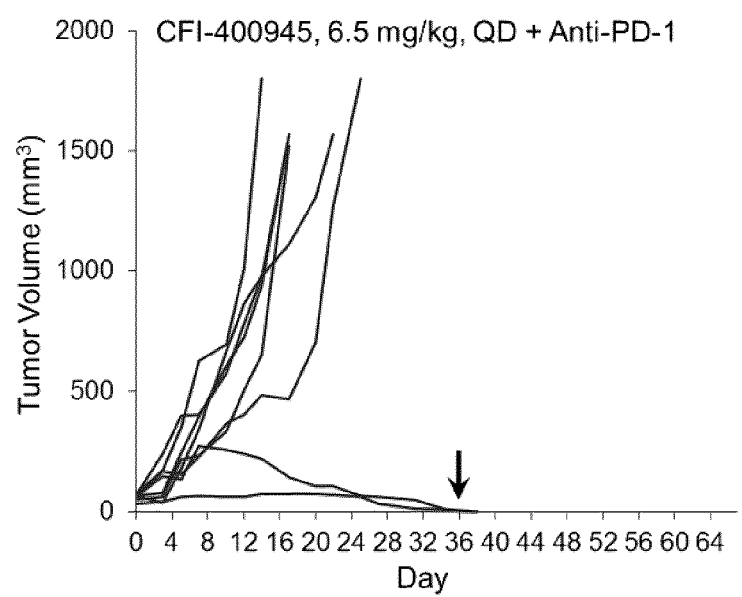
FIG. 1D illustrates change in CT26 tumor volume in Balb/cJ mice that received the combination of 150 μg of rat IgG2a anti-PD-1 antibody on Days 0, 3, 6 and 10 and 6.5 mg/kg of CFI-400945 once daily for 21 days. Animals in which complete tumor regression had occurred were re-challenged by inoculation with CT26 cells on Day 36 as indicated by the arrow.

Surprisingly, in the combination anti-PD-1-antibody and CFI-400945-treated arm of FIG. 1D, two of eight tumors completely regressed (CFI-400945 dosage=6.5 mg/kg once daily for 21 days).

Figure 1E:
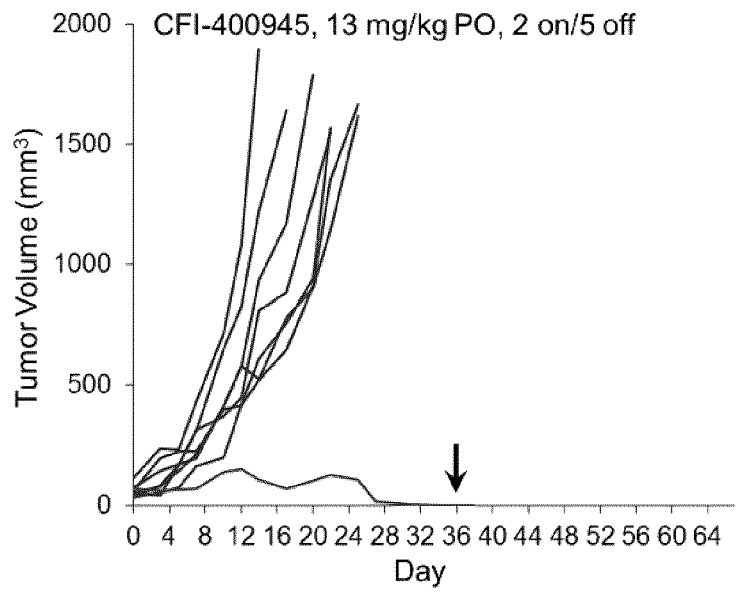
FIG. 1E illustrates change in CT26 tumor volume in Balb/cJ mice that received 13 mg/kg of CFI-400945 twice a week (2 days on/5 days off) for 21 days. Animals in which complete tumor regression had occurred were re-challenged by inoculation with CT26 cells on Day 36 as indicated by the arrow.
Figure 1F:
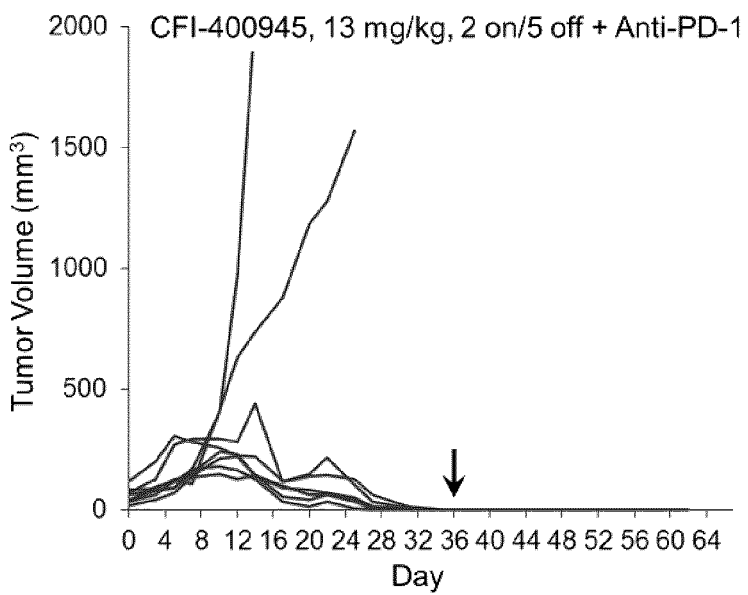
FIG. 1F illustrates change in CT26 tumor volume in Balb/cJ mice that received the combination of 150 μg of rat IgG2a anti-PD-1 antibody on Days 0, 3, 6 and 10 and 13 mg/kg of CFI-400945 twice a week (2 days on/5 days off) for 21 days. Animals in which complete tumor regression had occurred were re-challenged by inoculation with CT26 cells on Day 36 as indicated by the arrow.

At the CFI-400945 dosage of 13 mg/kg twice a week for 21 days (dosage well-tolerated), regression was observed in one of the eight tumors that underwent the monotherapy (FIG. 1E). Comparatively and notably, regression was observed in six of the eight tumors when the same CFI-400945 dosage was combined with the anti-PD-1-antibody (FIG. 1F).

Figure 1G:
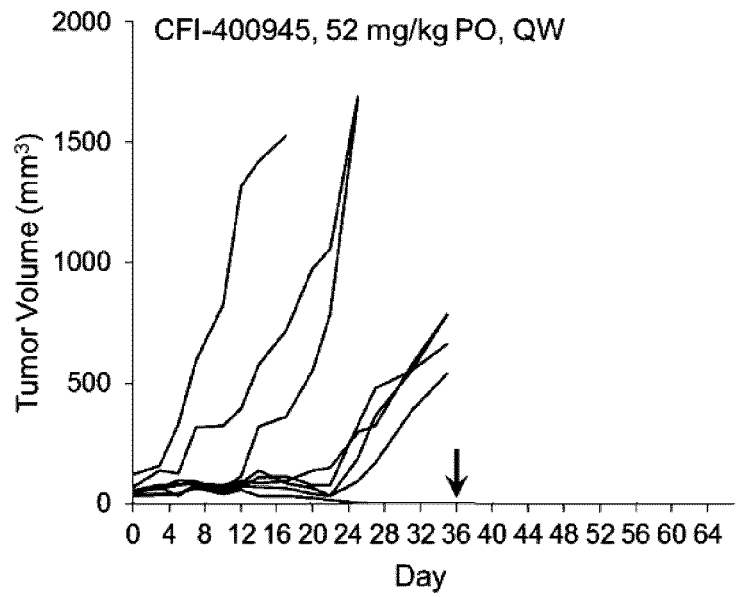
FIG. 1G illustrates change in CT26 tumor volume in Balb/cJ mice that received 52 mg/kg of CFI-400945 once weekly for 21 days. Animals in which complete tumor regression had occurred were re-challenged by inoculation with CT26 cells on Day 36 as indicated by the arrow.
Figure 1H:
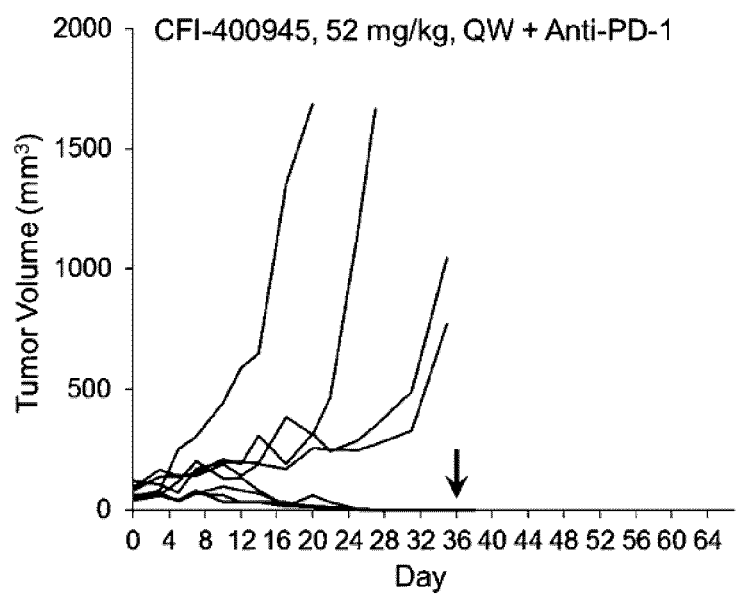
FIG. 1H illustrates change in CT26 tumor volume in Balb/cJ mice that received the combination of 150 μg of rat IgG2a anti-PD-1 antibody on Days 0, 3, 6 and 10 and 52 mg/kg of CFI-400945 once weekly for 21 days. Animals in which complete tumor regression had occurred were re-challenged by inoculation with CT26 cells at Day 36 as indicated by the arrow.
Figure 1I:
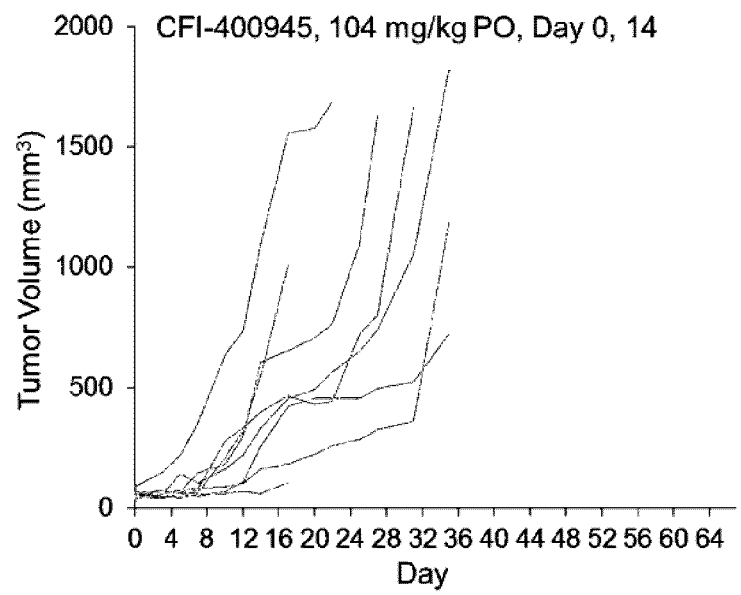
FIG. 1I illustrates change in CT26 tumor volume in Balb/cJ mice that received 104 mg/kg of CFI-400945 on Days 0 and 14.
Figure 1J:
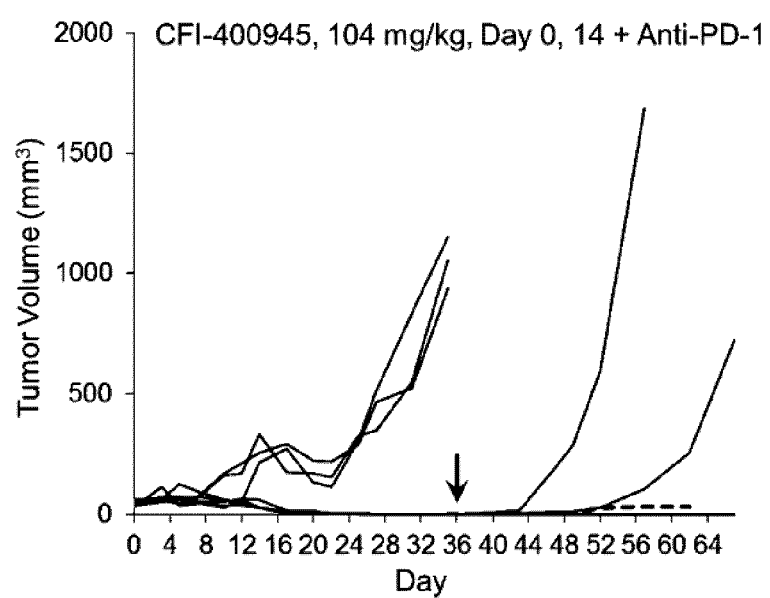
FIG. 1J illustrates change in CT26 tumor volume in Balb/cJ mice that received the combination of 150 μg of rat IgG2a anti-PD-1 antibody on Days 0, 3, 6 and 10 and 104 mg/kg of CFI-400945 on Days 0 and 14. Animals in which complete tumor regression had occurred were re-challenged by inoculation with CT26 cells at Day 36 as indicated by the arrow.

At the CFI-400945 dosage of 52 mg/kg once weekly for 21 days (dosage well-tolerated), regression was observed in one of the eight tumors that underwent the monotherapy (FIG. 1G). Comparatively and notably, regression was observed in four of the eight tumors when the same CFI-400945 dosage was combined with the anti-PD-1-antibody (FIG. 1H).

With two animals found dead, the CFI-400945 dosage of 104 mg/kg on Days 0 and 14 was found to not be well-tolerated. The plotted treatment arms for the CFI-400945 dosage of 104 mg/kg on Days 0 and 14, alone or in combination with anti-PD-1 antibody, are provided in FIGS. 1I and 1J, respectively.

Example 4

CFI-400945 and Anti-PD-1-Antibody Generates Tumor Immunity

Further to the tumor volume measurements, the animals in which complete regression had occurred as described above, either by CFI-400945 monotherapy or by IgG2a anti-PD-1 antibody-CFI-400945 combination therapy, were re-challenged by inoculation with CT26 cells on Day 36, as shown in FIGS. 1D (6.5 mg/kg QD CFI-400945+anti-PD-1 antibody), 1E (13 mg/kg BIW CFI-400945), 1F (13 mg/kg BIW CFI-400945+anti-PD-1 antibody), 1G (52 mg/kg QW CFI-400945), 1H (52 mg/kg QW CFI-400945+anti-PD-1 antibody) and 1J (104 mg/kg CFI-400945 on Days 0 and 14+anti-PD-1 antibody). With the exception of the combination therapy where the dosage of CFI-400945 was 104 mg/kg on Days 0 and 14 (FIG. 1J), tumors did not grow in any mouse, indicating that immunity to the CT26 cells had been generated. Meanwhile, as expected, the CT26 tumors in the control experiment also exhibited no immunity when challenged again with the same cells (FIG. 1A).

Example 5

MC38 Experiments

Established MC38 tumors were tested against various monotherapies and combination therapies.

Figure 2A:
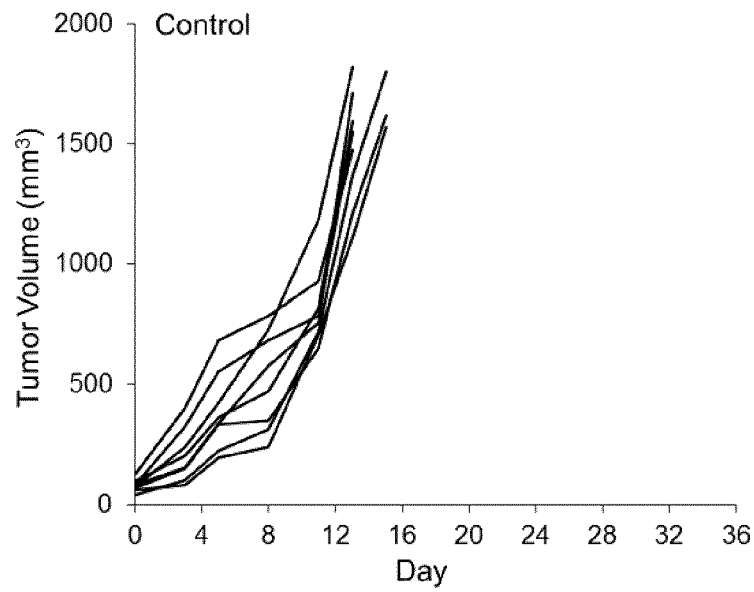
FIG. 2A illustrates change in MC38 tumor volume in C57BL/6 mice that received rat IgG2a isotype control.
Figure 2B:
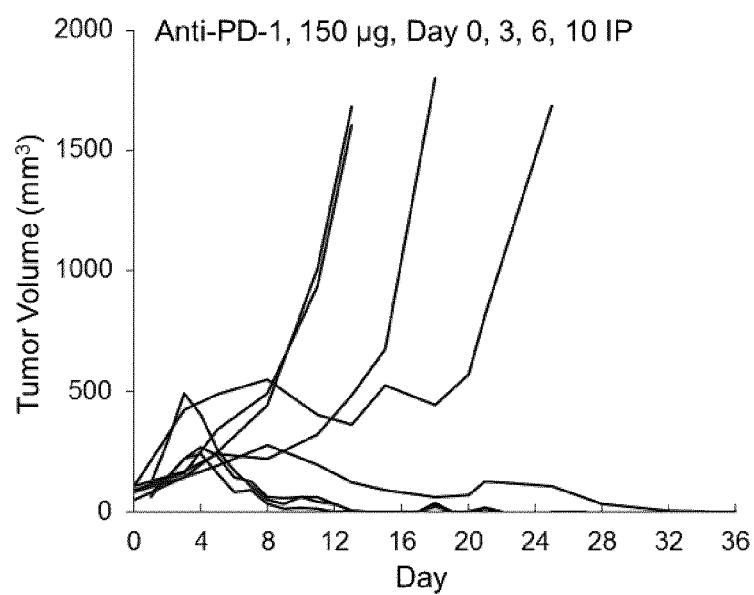
FIG. 2B illustrates change in MC38 tumor volume in C57BL/6 mice that received 150 μg of rat IgG2a anti-PD-1 antibody on Days 0, 3, 6 and 10.
Figure 2C:
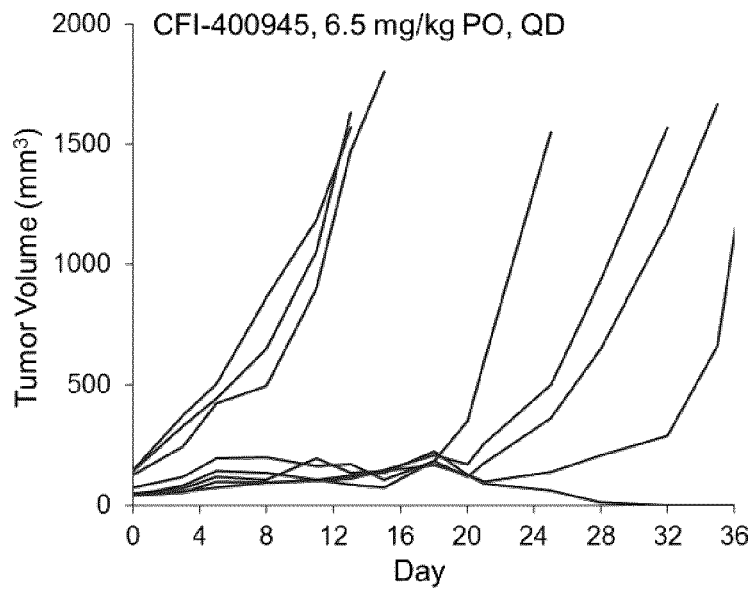
FIG. 2C illustrates change in MC38 tumor volume in C57BL/6 mice that received 6.5 mg/kg of CFI-400945 once daily for 21 days.
Figure 2D:
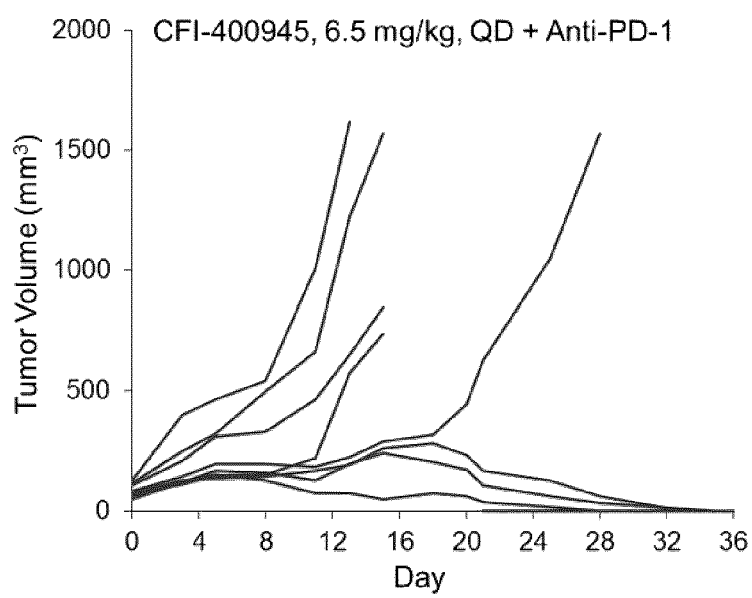
FIG. 2D illustrates change in MC38 tumor volume in C57BL/6 mice that received the combination of 150 μg of rat IgG2a anti-PD-1 antibody on Days 0, 3, 6 and 10 and 6.5 mg/kg of CFI-400945 once daily for 21 days.
Figure 3A:
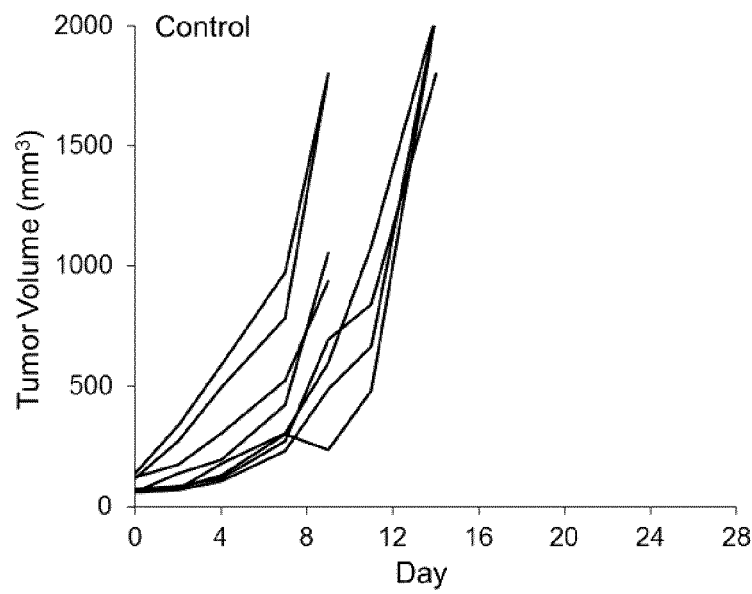
FIG. 3A illustrates change in MC38 tumor volume in C57BL/6 mice that received rat IgG2a isotype control.
Figure 3B:
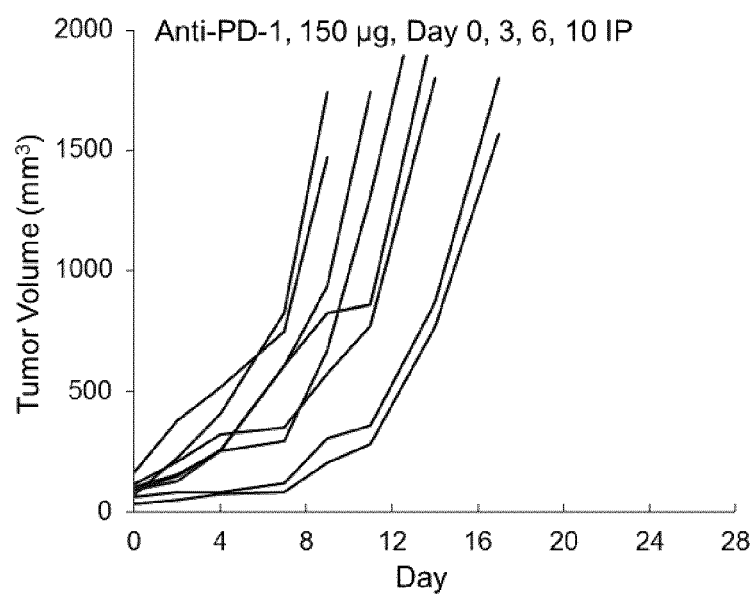
FIG. 3B illustrates change in MC38 tumor volume in C57BL/6 mice that received 150 μg of rat IgG2a anti-PD-1 antibody on Days 0, 3, 6 and 10.
Figure 3C:
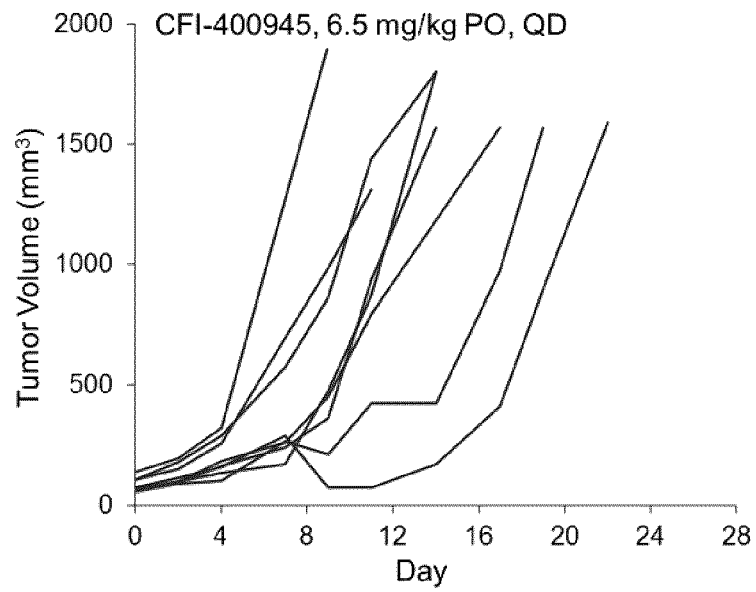
FIG. 3C illustrates change in MC38 tumor volume in C57BL/6 mice that received 6.5 mg/kg of CFI-400945 once daily for 21 days.
Figure 3D:
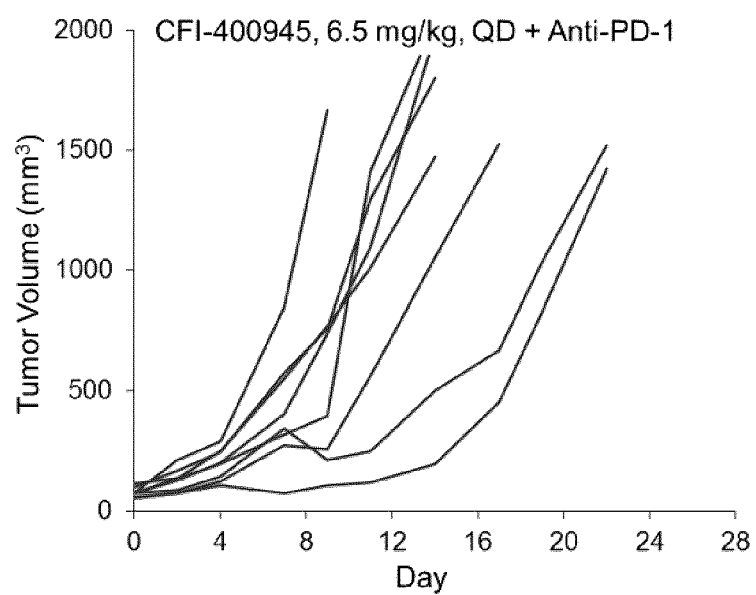
FIG. 3D illustrates change in MC38 tumor volume in C57BL/6 mice that received the combination of 150 μg of rat IgG2a anti-PD-1 antibody on Days 0, 3, 6 and 10 and 6.5 mg/kg of CFI-400945 once daily for 21 days.

In the first batch of MC38 experiments (FIGS. 2A-2D), the anti-PD-1-antibody monotherapy was found to efficaciously result in complete regression in four of the eight tumors (FIG. 2B). Regression was also observed in CFI-400945 monotherapy (FIG. 2C), in addition to IgG2a anti-PD-1 antibody-CFI-400945 combination therapy (FIG. 2D,).

In the second batch of MC38 experiments (FIGS. 3A-3D), however, no tumor regression was observed in any of the designed monotherapies and combination therapy.

While the applicants have described a number of embodiments of this invention, it is apparent that these basic examples may be altered to provide other embodiments that utilize the compounds and methods of this invention. Therefore, it will be appreciated that the scope of this invention is to be defined by the appended claims rather than by the specific embodiments that have been represented by way of example.

What is claimed is:

1. A method for treating colon cancer, comprising:
   administering to a subject an effective amount of a compound represented by the formula:

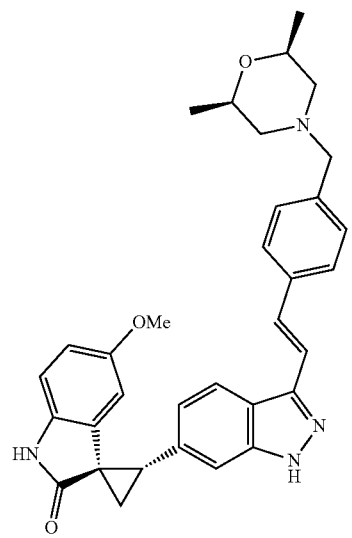 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

or a pharmaceutically acceptable salt thereof and an effective amount of a PD-1 inhibitor.

2. The method according to claim 1, wherein the PD-1 inhibitor is an antibody or an antigen binding fragment thereof.

3. The method according to claim 1, wherein the PD-1 inhibitor is a monoclonal antibody or an antigen binding fragment thereof.

4. The method according to claim 1, wherein the PD-1 inhibitor restores anti-tumor T-cell activity.

5. The method according to claim 1, wherein the PD-1 inhibitor blocks T-cell-inhibitory cell activity.

6. The method according to claim 1, wherein the PD-1 inhibitor is one selected from pembrolizumab, and nivolumab.

7. The method according to claim 1, wherein the PD-1 inhibitor is one selected from JS001, SHR-1210, BGB-A317, IBI-308 and REGN2810.

8. A method for treating colon cancer, comprising:
   administering to a subject an effective amount of a compound represented by the formula:

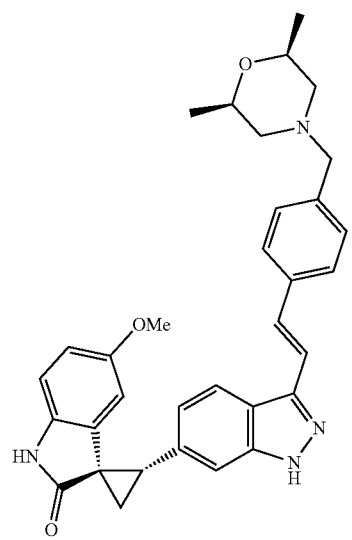 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

or a pharmaceutically acceptable salt thereof and an effective amount of durvalumab.

* * * * *